United States Patent [19]

Mumcu et al.

[11] Patent Number: 6,149,836

[45] Date of Patent: *Nov. 21, 2000

[54] LIQUID SOLUTIONS OF DICARBOXYLIC ACIDS

[75] Inventors: Salih Mumcu, Marl; Franz-Erich Baumann, Duelmen, both of Germany

[73] Assignee: Huels Aktiengesellschaft, Marl, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/724,505

[22] Filed: Sep. 30, 1996

[30] Foreign Application Priority Data

Sep. 28, 1995 [DE] Germany ............................ 195 36 056

[51] Int. Cl.⁷ ....................................................... C09K 3/00

[52] U.S. Cl. ......................................................... 252/182.28

[58] Field of Search .......................................... 252/182.28

[56] References Cited

U.S. PATENT DOCUMENTS

| | | | |
|---|---|---|---|
| 3,580,857 | 5/1971 | Cheng et al. | 252/182.28 |
| 3,882,085 | 5/1975 | Schmitt et al. | 528/229 |
| 3,935,155 | 1/1976 | Osmond et al. | 524/504 |
| 4,898,896 | 2/1990 | Maj et al. | 528/323 |
| 5,068,311 | 11/1991 | Horn et al. | 528/324 |
| 5,169,582 | 12/1992 | Illing | 264/141 |
| 5,298,598 | 3/1994 | Yuo et al. | 528/336 |
| 5,310,905 | 5/1994 | Moran | 540/540 |
| 5,405,936 | 4/1995 | Mumcu et al. | |
| 5,416,172 | 5/1995 | Blondel et al. | 525/432 |
| 5,422,418 | 6/1995 | Maj et al. | 528/324 |
| 5,696,227 | 12/1997 | Mumcu | 528/318 |

*Primary Examiner*—Edward A. Miller
*Attorney, Agent, or Firm*—Oblon, Spivak, McClelland, Maier & Neustadt, P.C.

[57] ABSTRACT

Liquid melts of dicarboxylic acid have a tendency to undergo unwanted discoloration on prolonged storage. By means of a solution of the dicarboxylic acids in a lactam of an aliphatic $\alpha,\omega$-aminocarboxylic acid, the discoloration can be avoided.

16 Claims, 3 Drawing Sheets

LIQUID SOLUTIONS OF DICARBOXYLIC ACIDS

BACKGROUND OF THE INVENTION

Field of the Invention

The invention relates to liquid solutions of dicarboxylic acids having 6 to 44 carbon atoms.

Discussion of the Background

A wide area of application for dicarboxylic acids is their use, for example, as a raw material in the preparation of polyamides. An inexpensive preparation process, which eliminates the quantities of water required in the conventional procedure via nylon salt solutions, is to start from melted diamines and dicarboxylic acids. In this case the components are melted, mixed and subjected in the melt to polycondensation. In practice, an important disadvantage of the process is that the dicarboxylic acid cannot be melted without discoloration, and becomes severely discolored on prolonged storage in the melted state. This discoloration is then passed onto the polyamide produced by polycondensation. A product of this kind is not accepted in the market. Aromatic dicarboxylic acids, for example terephthalic acid, cannot be melted at all without undergoing decomposition.

In practice, therefore, polycondensation in the aqueous phase is chosen instead. On the industrial scale, this process requires the heating and evaporation of large quantities of water (EP-A-0 122 005).

For these reasons it is desirable to find practicable ways of carrying out the polycondensation in the melt. The object of the invention was to provide an aliphatic dicarboxylic acid, in the form of a liquid melt, which shows no discoloration even on prolonged storage.

SUMMARY OF THE INVENTION

The problem highlighted is overcome by dissolving the dicarboxylic acid in a lactam of an aliphatic α,ω-aminocarboxylic acid having 6 to 16 carbon atoms.

DESCRIPTION OF THE PREFERRED EMBODIMENTS

Figure 1:
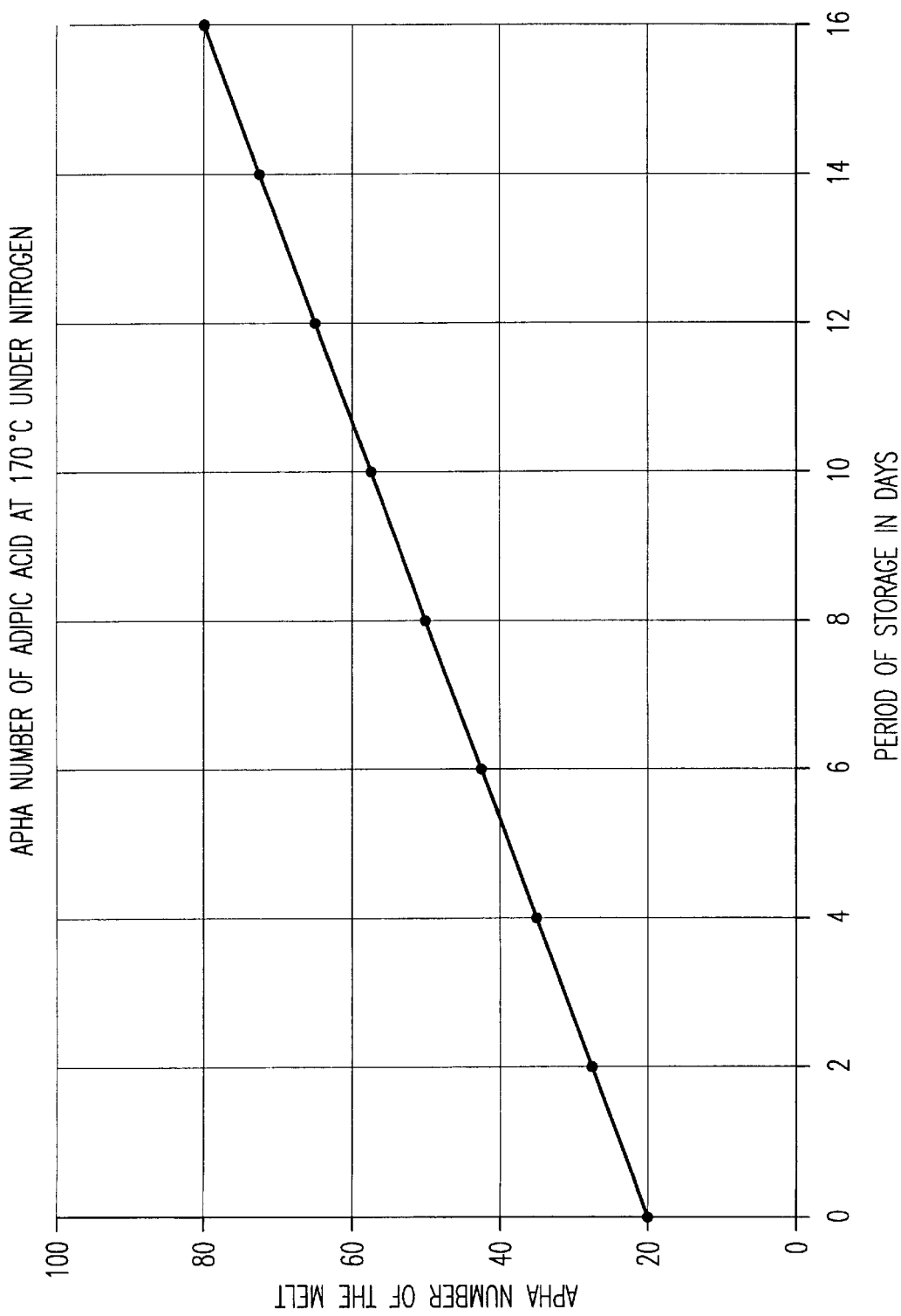

Suitable lactams are those derived from an aliphatic α,ω-aminocarboxylic acid having 6 to 16, preferably 6 to 12, carbon atoms. Particular mention may be made of 6-hexanelactam (ε-caprolactam), 12-dodecanelactam (laurolactam), 8-octanelactam, 10-decanelactam, 7-heptanelactam and 9-nonanelactam. Mixtures of lactams can also be employed.

Dicarboxylic acids which can be employed are aliphatic, cycloaliphatic and aromatic dicarboxylic acids having 6 to 44, preferably 6 to 13, carbon atoms. Examples which may be mentioned are adipic acid, suberic acid, azelaic acid, sebacic acid, undecanedicarboxylic acid, dodecanedicarboxylic acid, dimerized fatty acids, brassylic acid, cyclohexanedicarboxylic acid, terephthalic acid, isophthalic acid, 2,6-naphthalenedicarboxylic acid and/or 4,4'-biphenyldicarboxylic acid.

The liquid dicarboxylic acid solutions according to the invention are generally prepared by adding the solid dicarboxylic acid to the liquid lactam until a clear solution has been obtained. However, preparation is not limited to the procedure indicated. Any other technically reasonable procedure can be applied with the same success.

It is possible to dissolve up to 4 times the amount, preferably up to 1.5 times the amount—based on the weight of lactam—of dicarboxylic acid in the lactam.

For storage, as low a temperature as possible is the aim. Temperatures which have been found advantageous are those in the range from 60 to 160° C., preferably from 100 to 140° C.

The liquid solutions according to the invention are particularly suitable as starting material for the preparation of polyamides, including copolyamides. In this way, large quantities of product can be stored in liquid form over a number of days without discoloration occurring in the solution or in the capolyamide prepared therefrom. At the same time, it has surprisingly been found that the lactam present in the solution—even if water is present—shows no tendency to form insoluble polycondensation products.

Where the solutions according to the invention are to be employed as starting material for polyamide preparation, it is advisable to establish a quantitative ratio of dicarboxylic acid to lactam which is the same as that necessary for polyamide.

The parameters mentioned are determined with the aid of the following measuring techniques.

The solution viscosity (rel. viscosity $\eta_{rel}$) of the polyamides is determined using a 0.5% strength by weight m-cresol solution at 25° C. (DIN 53 727/ISO 307).

The melting temperature is determined by DSC (ASTM D 3408).

The APHA color number is determined in cuvettes (height: 300 mm - diameter: 25 mm) on a methanolic solution (20% by weight) in daylight, this solution being compared with aqueous solutions of $CoCl_2$ and $K_2PtCl_6$ in various concentrations as color standards (DIN 53 409).

Having generally described this invention, a further understanding can be obtained by reference to certain specific examples which are provided herein for purposes of illustration only and are not intended to be limiting unless otherwise specified.

Examples identified with letters are not according to the invention.

EXAMPLES

Example A 2.5 kg of adipic acid are degassed in a 5 l steel autoclave with blade stirrer and bottom valve, and are then heated at 170° C. under a $N_2$ atmosphere. Samples are taken every 2 days; the increase in the APHA color number over 16 days is shown in FIG. 1.

Example 1

Figure 2:
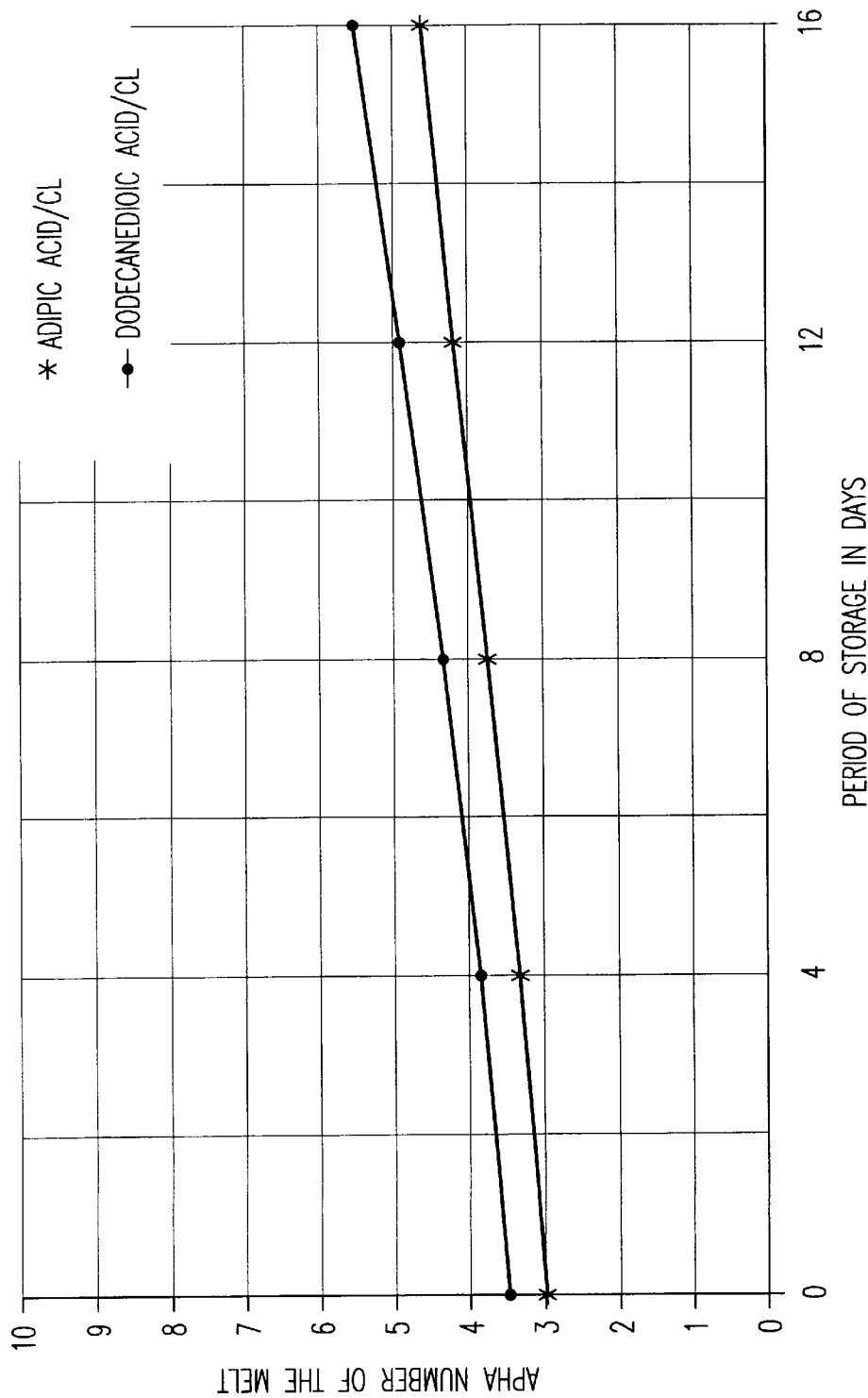

A mixture of 40% by weight adipic acid and 60% by weight caprolactam is treated as in Example A but at 115° C. At this temperature, the mixture has melted completely. The change in color number over 16 days is shown in FIG. 2.

Example B

Figure 3:
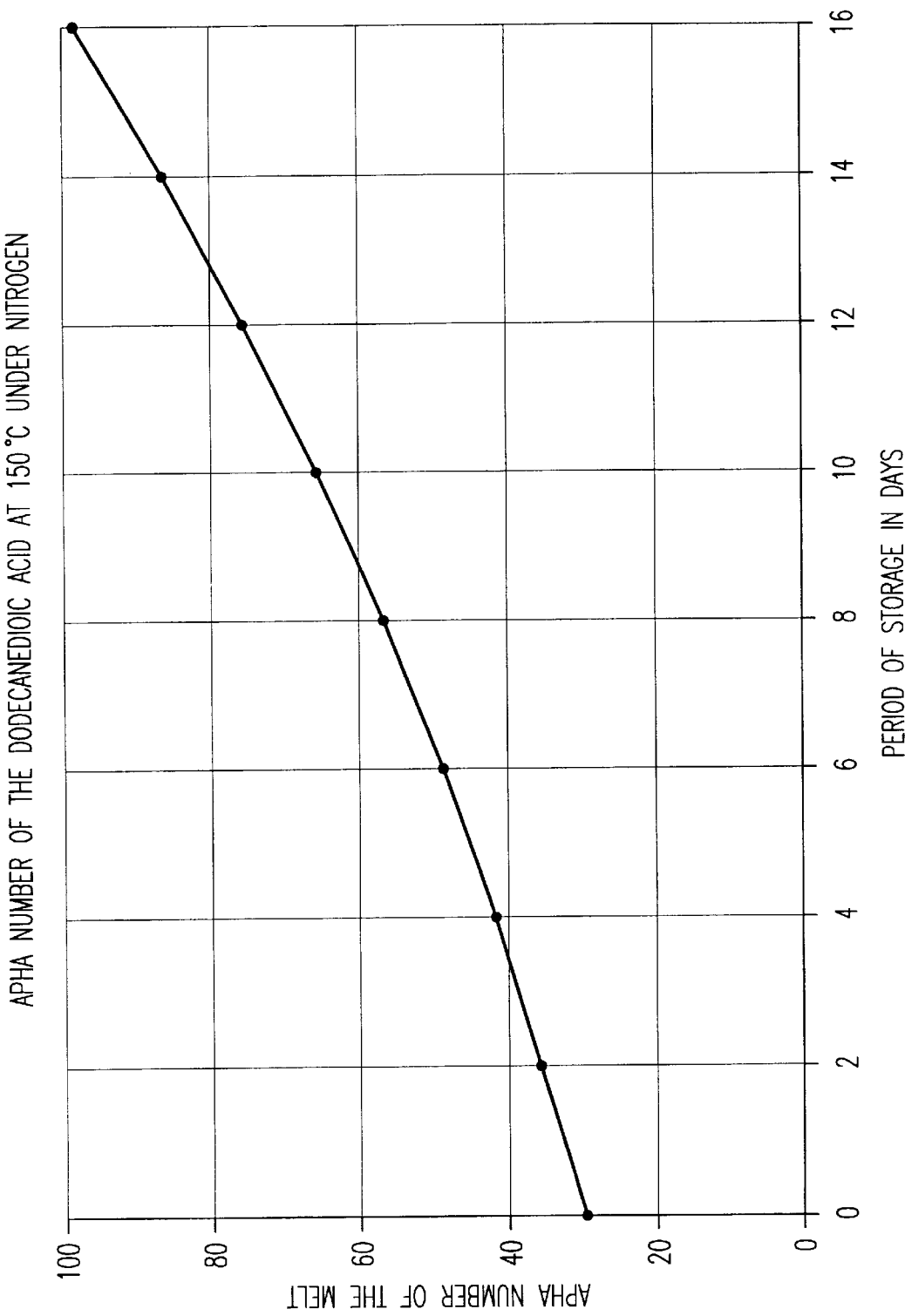

In accordance with Example A, dodecanedioic acid is left at 150° C. for 16 days. FIG. 3 shows the increase in the APHA color number during this period.

Example 2

Example 1 is repeated with a mixture of 40% by weight dodecanedioic acid and 60% by weight caprolactam; see FIG. 2.

Example C 49.50 kg of laurolactam are placed in a polycondensation vessel. Then 28.89 kg of dodecanedioic acid are introduced under pressure, from a stock tank maintained at a storage temperature of 150° C., into the polycondensation vessel. Simultaneously, 21.61 kg of 1,10-decanediamine are heated to 80° C. under nitrogen in a melting vessel, stirred for 2 h and introduced under pressure through a 90 μm filter into the polycondensation vessel. The mixture is then heated to 235° C. over the course of 3 h with stirring and left at this temperature for 1 h, and the melt is then brought to 280° C. with continuous release of pressure. The melt is let down to atmospheric pressure over the course of 1.5 h, nitrogen is passed over it for ½ h, and the melt is then discharged as extruded granules. 93.60 kg of honey-yellow granules are obtained; $\eta_{rel}$=1.79; melting point: 163° C.

An 80 μm flat film is extruded from these granules. This film has an intrinsic yellow color, streaks and specks.

Example 3:

A mixture of 63.15 parts by weight of laurolactam and 36.85 parts by weight of dodecanedioic acid is stored in a storage tank at 115° C. 78.386 kg of this mixture are introduced under pressure into a polycondensation vessel. In a melting vessel, 21.613 kg of 1,10-decanediamine are heated to 80° C. under nitrogen and stirred for 2 h. The subsequent procedure is as in Example C. 93.57 kg of colorless granules are obtained; $\eta^{rel}$=1.86; melting point: 165° C.

The 80 μm flat film extruded from these granules is colorless and free of streaks and specks.

The disclosure of German Priority Patent Application 195 36 056.7, filed Sep. 28, 1995, is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A liquid melt composition suitable for storage at 60–160° C., consisting essentially of an aliphatic or cycloaliphatic dicarboxylic acid having 6 to 44 carbon atoms in a lactam of an aliphatic α,ω-aminocarboxylic acid having 6 to 16 carbon atoms.

2. A method of preparing a liquid melt composition, comprising:

forming in a storage tank a mixture consisting essentially of a dicarboxylic acid having 6 to 44 carbon atoms and a lactam of an aliphatic α, ω-aminocarboxylic acid having 6 to 16 carbon atoms, and maintaining said mixture at a temperature of 60–160° C. for at least two days.

3. The method of claim 2, wherein the dicarboxylic acid has 6 to 13 carbon atoms.

4. The method of claim 2, wherein the dicarboxylic acid is adipic acid, suberic acid, sebacic acid, azelaic acid, brassylic acid and/or dodecanedioic acid.

5. The method of claim 2, wherein the dicarboxylic acid is terephthalic acid, isophthalic acid, 2,6-naphthalenedicarboxylic acid and/or 4,4'-biphenyldicarboxylic acid.

6. The method of claim 2, wherein the lactam of the aliphatic α,ω-aminocarboxylic acid has 6 to 12 carbon atoms.

7. The method of claim 3, wherein the lactam of the aliphatic α,ω-aminocarboxylic acid has 6 to 12 carbon atoms.

8. The method of claim 4, wherein the lactam of the aliphatic α,ω-aminocarboxylic acid has 6 to 12 carbon atoms.

9. The method of claim 5, wherein the lactam of aliphatic α,ω-aminocarboxylic acid has 6 to 12 carbon atoms.

10. The method of claim 2, wherein the lactam is 6-hexanelactam (ε-caprolactam), 12-dodecanelactam (laurolactam), 8-octanelactam, 10-decanelactam, 7-heptanelactam and/or 9-nonanelactam.

11. The method of claim 3, wherein the lactam is 6-hexanelactam (ε-caprolactam), 12-dodecanelactam (laurolactam), 8-octanelactam, 10-decanelactam, 7-heptanelactam and/or 9-nonanelactam.

12. The method of claim 3, wherein the lactam is 6-hexanelactam (ε-caprolactam), 12-dodecanelactam (laurolactam), 8-octanelactam, 10-decanelactam, 7-heptanelactam and/or 9-nonanelactam.

13. The method of claim 5, wherein the lactam is 6-hexanelactam (ε-caprolactam), 12-dodecanelactam (laurolactam), 8-octanelactam, 10-decanelactam, 7-heptanelactam and/or 9-nonanelactam.

14. The method of claim 2, wherein up to 4 times the amount of dicarboxylic acid is present, based on the weight of lactam.

15. The method of claim 14, wherein up to 1.5 times the amount of dicarboxylic acid is present, based on the weight of lactam.

16. The method of claim 2 wherein said mixture is maintained for at least two days at a temperature in the range from 100 to 140° C.

* * * * *